United States Patent [19]

Craighead

[11] Patent Number: 4,848,348

[45] Date of Patent: Jul. 18, 1989

[54] COATED FILMS

[75] Inventor: Lawrence W. Craighead, Medota Heights, Minn.

[73] Assignee: Minnesota Mining and Manufacturing Company, St. Paul, Minn.

[21] Appl. No.: 865,522

[22] Filed: May 21, 1986

Related U.S. Application Data

[63] Continuation-in-part of Ser. No. 551,069, Nov. 14, 1983, Pat. No. 4,640,289.

[51] Int. Cl.$^4$ .............................................. A61B 5/04
[52] U.S. Cl. .................................... 128/639; 128/798; 428/323; 428/325; 428/328; 428/329; 428/331; 428/336; 428/425.8; 428/425.9; 428/458; 428/480
[58] Field of Search ............... 428/458, 323, 325, 329, 428/328, 331, 336, 480, 425.8, 425.9; 427/131, 44; 128/639, 640, 798, 641

[56] References Cited

U.S. PATENT DOCUMENTS

| | | | |
|---|---|---|---|
| 3,595,720 | 7/1971 | Graham | 156/47 |
| 3,764,280 | 10/1973 | Lupinski et al. | 428/425.9 |
| 3,830,656 | 8/1974 | Takenaka et al. | 428/425.9 |
| 3,847,649 | 11/1974 | Sova | 428/458 |
| 3,852,151 | 12/1974 | Knapp | 428/458 |
| 3,900,654 | 8/1975 | Stinger | 156/47 |
| 4,123,277 | 10/1978 | Ochiai | 96/85 |
| 4,247,496 | 1/1981 | Kawakami | 264/22 |
| 4,348,446 | 9/1982 | Mitsuishi | 428/148 |
| 4,404,237 | 9/1983 | Eichelberger et al. | 427/96 |
| 4,493,872 | 1/1985 | Funderbunk et al. | 428/458 |
| 4,540,618 | 9/1985 | Suzuki et al. | 428/327 |
| 4,578,310 | 3/1986 | Hatfield | 428/425.8 |
| 4,596,747 | 6/1986 | Nishimatsu et al. | 428/900 |
| 4,619,856 | 10/1986 | Kamada et al. | 427/131 |
| 4,621,995 | 6/1987 | Sekiya et al. | 428/425.9 |
| 4,623,481 | 11/1986 | Hoybrechts et al. | 523/427 |
| 4,666,769 | 5/1987 | Miyata et al. | 427/131 |

FOREIGN PATENT DOCUMENTS 81301253.1 3/1981 European Pat. Off.
81305262.8 11/1981 European Pat. Off.
2026344A 6/1979 United Kingdom.

OTHER PUBLICATIONS

"Adhesion Aspects of Polymeric Coatings", K. L. Mittal, ed. pp. 3–44, 107–113 and 265–280 (1984).

Primary Examiner—George F. Lesmes
Assistant Examiner—James B. Monroe
Attorney, Agent, or Firm—Donald M. Sell; Walter N. Kirn; Dale E. Hulse

[57] ABSTRACT

Films coated with a primer and an adhered layer of metal, metal oxide, metal salt, semiconductor material are shown. The primer is comprised of binder and powder particles and is coated to a dry thickness between 1 micron and 100 microns. The powder particles have a median effective spherical diameter between 0.5 microns and 100 microns.

25 Claims, 1 Drawing Sheet

COATED FILMS

This application is a continuation-in-part of co-pending application Ser. No. 551,069, filed Nov. 14, 1983, (now U.S. Pat. No. 4,640,284) the entire contents of which is hereby incorporated by reference. The invention relates to coated polymeric films. More particularly it relates to polymeric films coated with a primer coat and having an adhered coating of metal, metal oxides, metal salts, or semiconductor material.

BACKGROUND

Deposition of metals, metal salts, metal oxides, and semiconductor materials on conformable substrates is well known. These coated films are used for example as electrical conductors, magnetic recording media, imaging films and decorative films. Coated films are also well known for flaking, cracking, crazing, and delamination. Mechanical handling of the films in manufacturing and in use frequently results in damage to the metal coating. Various techniques have been proposed to increase adhesion to substrate of metals and their salts and oxides, and of semiconductor materials.

Various mechanisms of surface adhesion of metal to substrate and of resins and polymers to metals are explored in "Adhesion Aspects of Polymeric Coatings" K. L. Mittal, ed. pp. 3–44, 107–113, and 265–280 (1984). Acid base interactions and surface topography are reviewed with the conclusion that the mechanisms of adhesion are not clearly understood. The authors examine the peel effect in polymeric coatings of strain caused by internal shrinkage. They observe that a coating will spontaneously detach from its substrate when the strain energy per unit area in the coating is equal to or greater than the interfacial work of adhesion. They examine the relationship between cohesive forces and interfacial strength to observe that an interfacial strength exceeding the cohesive strength will result in cracking and crazing rather than adhesive failure. Water stability of adhesion between polymers and metals is examined. Three surface characteristics are identified as relevant: physical and chemical reactivity or surface energy, morphology, and mechanical properties. The authors conclude that chemical bonds between polymers and metal surfaces alone cannot account for the water stability of adhesion. Surface treatments such as Chemoxal etching chromic sulfuric acid etching, sand blasting, phosphoric acid anodizing, chromic acid anodizing, ion bombardment etching and sulfuric acid anodizing are identified as methods to alter the micromorphology of surfaces and influence micromechanical mechanism of adhesion.

European patent application No. 81.301253.1 discloses decorative films and suggests vacuum deposition of discrete islands of metal particles on a smooth surface and thereafter coating the film with a protective top coat. These nonconductive films are said to withstand flexing and bending without microcracking because the metal exists as discrete particles on the film.

European Patent Appl. No. 81.305262.8 discloses polymeric surfaces which are pitted by penetrating the surface with a first reactant and thereafter with a second reactant. The second reaction reacts with the first reactant to produce pits in the film without substantially degrading the film between the pits. The first reactant is preferably an organic solvent that penetrates the film without swelling. The second reactant is preferably a chemical etchant that reacts preferentially with first reactant rather than the film.

U.S. Pat. No. 4,348,446 describes a polyester film which has been treated to be free of interfacial sticking during winding and to have excellent abrasion resistance. The film has microscopic protrusions on its surface and is prepared by adding inert particles in the coarse (1.5 to 2.5 microns), intermediate (0.5 to 1.5 microns), and very fine (less than 0.5 microns) diameter size ranges. The inert particles may be MgO, ZnO, $MgO_3$, $CaCO_3$, $CaSO_4$, $BaSO_4$, $Al_2O_3$, $SiO_2$, $TiO_2$ or the calcium or manganese salts, terephthalic acid, koalin, china clay, diatomaceous earth, alumina silicates, their hydrates, carbon black, or calcium phosphate. The inert particles are added to the polyester prior to polymerization, during polymerization, at the pelletizing stage, in the extruder after polymerization, or when the polyester is molten for extrusion. The film thus prepared is recommended for use as a base film for magnetic recording tape.

U.K. Patent Application No. 2,026,344 describes a polyester magnetic recording tape with micro roughness. Micro roughness is achieved by adding particles of calcium stearate, calcium acetate, or a calcium salt of a polyethylene terephthalate oligomer before or during condensation. Alternatively particles of inorganic substances such as kaolin and calcium carbonate may be incorporated into the polycondensation reaction mixture or into molten polyethylene terephthalate during film forming. The magnetic layer may be any of the conventional magnetic materials and a binder resin.

U.S. Pat. No. 4,247,496 discloses stretching a thermoplastic polymeric film and irradiating the film during or after stretching with UV light. The treatment is said to improve surface properties such as strip, oil impregnation, durability and deluster.

U.S. Pat. No. 4,123,277 describes various treatments to improve adhesion of a hydrophilic photographic emulsion to a hydrophobic resin such as polyester. Surface treatments such as chemical treatment, flame treatment, UV light treatment, high frequency treatment, glow discharge treatment, active plasma treatment, and ultraviolet laser treatment and the deficiencies of these treatments are mentioned. Use of an emulsion polymers as a primer without any surface treatment is also described. One such primer is a copolymer of butadiene, an ethylenically unsaturated monomer carboxylic acid and one other ethylenically unsaturated copolymerizable therewith. It is coated on a polyester film. The precursors for the copolymer disclosed in that patent are a monomer containing an N-alkanolamide moiety or an N-alkoxyalkylamide moiety, a component which provides a carboxy group, and a hydrophobic monomer. The monomers are polymerized with a latex polymerization process in aqueous solvents. An aqueous solution of the melted polymer is coated on the film with improved adhesion. The photo emulsion layer is selected from any of the conventional synthetic and natural hydrophobic high molecular weight compounds and suspended material such as silica halide, physical development nuclei such as silver sulfide or noble metal colloids or light sensitive materials such as diazo compounds.

The foregoing examples of coated films illustrate the complex and expensive processes for improving adhesion of coatings to polymers. These techniques require large capital expenditures for equipment and inspection control. A low cost, high quality, low waste coated film is needed for many applications. One particular application is electrically conductive films to be used as connectors or as conductors in electrodes.

SUMMARY OF THE INVENTION

The present invention is a polymeric film coated on at least one surface with a primer and the primer is coated on the surface opposing the film with an adhered layer of one or more or a mixture of metal, metal oxide, metal salt, or semiconductor material. The primary should contain a binder and powder particles. The powder particles should have median equivalent spherical diameter between 0.5 micron to 100 microns. The dry thickness of the primer on the film should be between 0.5 micron and 100 microns.

The composite can be made very easily and inexpensively by simply printing or coating a primer solution comprised of binder, powder particles and solvent on the polymeric film, evaporating away the solvent and thereafter coating the adhered layer using such conventional techniques as vapor deposition, sputtering, plasma vacuum deposition, electroplating, or simply mechanically pressing the layer into the surface of the primer, for example, by calendering or hammering. Coated films incorporating a primer between the film and adhered layer exhibit improved adhesion when compared to the more exotic and expensive coated films of the prior art.

Especially preferred embodiments of the present invention use a polyester film coated with a primer comprised of particle materials which are at least 60 weight percent silicon carbide, at least 60 weight percent silver flakes or 60 weight percent graphite fibers and a binder which is either polyester resin or polyurethane resin. The adhered layer is a biocompatible conductor and a biocompatible salt. Silver/silver chloride or graphite is preferred. If it is silver/silver chloride, it contains at least 1.5 gm/m² silver, preferably 5.4 gm/m² silver, and at least 0.3 gm/m² silver chloride. The graphite coating contains at least 3.0 gm/m². These composites are very durable conformable films which can be used as electrical conductors in biomedical electrodes. The composite may replace conventional metal or metallized post and eyelet terminals used to connect the biomedical electrode to a monitoring or recording instrument. These composites may be used as an electrical conductors in electrodes which meet the standard for Defibrillation Overload Recovery published by the Association for the Advancement of Medical Instruments under the title "American National Statement for Pregelled ECG Disposable Electrodes" and approved by ANSI, Aug. 28, 1984. Surprisingly the silver/silver chloride composites of the present invention are X-Ray translucent even if the adhered layer of silver/silver chloride contains 16 gm/m² of silver. Because the adhesion of the adhered layer to the film is so strong, the composites may be used in high speed rotary manufacturing processes and in applications involving significant flexure.

DETAILED DESCRIPTION

Figure 1:
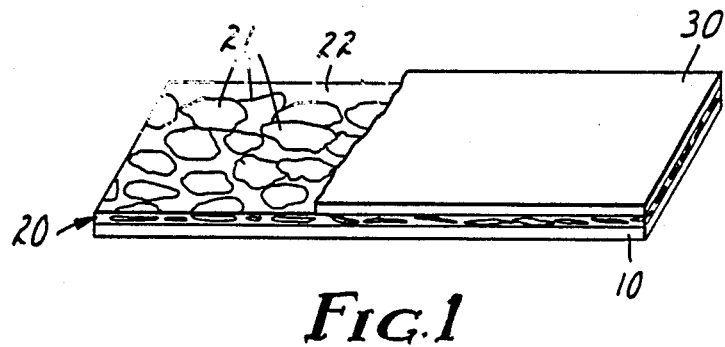
FIG. 1 is a perspective view of the composite of the present invention with the adhered coating layer broken away to more clearly show the primer layer.
Figure 2:
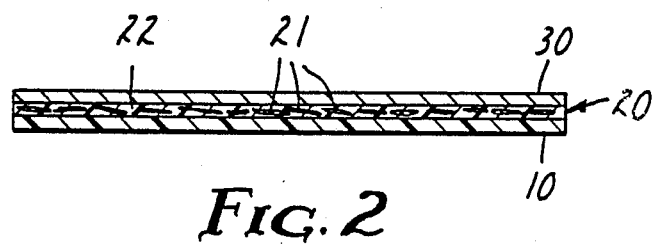
FIG. 2 is cross-section view of the composite of the present invention.

Referring to the figures, the composite of the present invention has a polymeric film 10, a primer layer 20, and an adhered layer 30. The primer layer has powder particles 21 suspended in binder 22.

The polymeric film may be made from any natural or synthetic polymeric resin. It may be rough or smooth, transparent, translucent or opaque, and continuous or porous. The resin may be a polyester (e.g., polyethylene terephthalate), a cellulose ester, a polycarbonate, a polyvinyl resin (e.g., polyvinylchloride, polyvinylidene chloride polyvinylbutyral, polyvinylformal), a polyamide, a polyimide, a polacrylate (e.g., copolymers and homopolymers of acrylic acid, methacrylic acid, n-butyl acrylate, acrylic anhydride and the like), a polyolefin, and the like. It may contain fillers such as carbon black, titania, zinc oxide, dyes, pigments, and of course, those materials generally used in the formation of films such as coating aids, lubricants, antioxidants, ultraviolet radiation absorbers, surfactants, catalysts, slip agents and the like. The preferred polymeric film is polyethylene terephthalate.

The binder material may be any polymeric resin of the types used for solvent coatings, hot melt extrusion coatings and resin powder coatings. Proprietary polyester copolymers sold by Goodyear Chemical, Akron, Ohio under the tradename VITEL ® are suitable. Resins for solvent based coatings include VITEL PE-200, VITEL PE-200D, VITEL PE-222. A resin suitable for hot melt extrusion is VITEL VPE-5571AG. A thermoset powder coating resin is VPE-5802A. Polyurethane resins of both the aromatic polyester- and polyether-based classes are also preferred. A suitable polyester based urethane is ESTANE ® polymer No. 5703 (B. F. Goodrich, Cleveland, Ohio), and suitable polyether based urethane are ESTANE polymer Nos. 5704 and 5715. Other suitable resins for use as binder material include vinylidene chloride-acrylonitrile copolymer, vinyl chloride homopolymer, vinyl chloride-vinylidene chloride copolymer, vinyl chloride-vinyl acetate copolymer, butadiene-acrylonitrile copolymer, bisphenol-epichlonihydrin-epoxy, bispheniol-epichlorohydrin copolymer, alkyl phenol novolak, melamine-formaldehyde resin, and urea-formaldehyde resin.

The powder particles may be selected from any of the naturally occurring or synthetic, organic and inorganic, fillers and pigments used in dyes, inks, and paints. Where the composite is intended to serve a particular function e.g., an electrical conductor, the powder particles incorporated into the binder may be selected to enhance the performance of the composite. Thus electrically conductive metals, or their salts or oxides may be used as the powder in the primer. Representative particles include aluminum, its nitride, carbide and oxide; crystalline and amorphous; boron, its carbide and nitride; cadmium metal powder; calcium oxide; chromium metal, its carbide and trioxide; cobalt metal powder; copper metal powder; inconel metal power; indium hydroxide; iron metal and its titanate; lead powder; manganese granules; electrolytic manganese metal powder; magnesium, its aluminate, oxide, and chromate; molybdenum and its oxide; nickel chromium alloy metal powder, nickel metal powder, and nickel oxide; palladium metal powder; silica; silicon, its carbide and nitride; stainless steel powder; tantalum metal; its carbide and oxide; tin metal powder, titanium, its diboride, carbide, and dioxide; tungsten and its trioxide; vanadium boride; zinc metal powder; and zirconium carbide. Synthetic and naturally occurring silicates may be used. Naturally occurring solid carbonaceous materials such as anthracites, butuminous, and sub-butuminous coals and lignites may be used as the powder particles. Cellulose materials such as wood pulp and fibers may be used. Clays may be used.

The preferred powder particles are silver, aluminum oxide, silicon carbide, and graphite. Silver, aluminum oxide and silicon carbide are preferably used in flake form. Graphite is preferably used as flakes.

Yet another preferred class of powder particles is microspheres. Microspheres may be coated with metal, e.g. silver, aluminum or with graphite. Coated microspheres of this type are described in U.S. Pat. No. 3,486,952. They are commercially available from Potters Industries, Inc., Carlstad, NJ.

The particles should have a median equivalent spherical diameter from about 0.5 microns to 100 microns. As used herein "median equivalent spherical diameter" refers to the median effective diameter as determined according to Stokes Law. One test for determining the equivalent spherical diameter is the "Standard Test Method For Average Particle Size of Powders of Refractory Metals and Their Compounds By the Fisher Sub-Sieve Sizer" ASTM B-330. Sedimentation and coulter counter tests are also well known methods for determining median equivalent spherical diameter. A coulter counter procedure is described in ASTM C-690-80. While that procedure is described for alumina or quartz it is suitable for other particles. The Horiba TM centrifugal particle size distribution analyzer, Model CAPA 500 (available from Horiba Instruments Inc., Irvine, Calif.) can be used to determine median effective spherical diameter by measuring sedimentation rates. The median equivalent spherical diameter may suitably be from about 1 micron to about 50 microns. Conveniently, the median equivalent diameter is from about 1 micron to about 40 microns. Preferably, the median equivalent spherical diameter is from 2 microns to 20 microns. Most preferred for silver is a median equivalent spherical diameter particle size of 2 microns. Most preferred for silicon carbide is a median effective spherical diameter of about 12 microns. Most preferred for graphite is a median effective spherical diameter of about 0.9 microns.

The ratio of dry binder to powder particles in the primer may vary from 99 percent by weight binder and 1 percent by weight powder particle to 1 percent by weight binder and 99 percent by weight powder particle. Suitable primers have between 95 percent by weight binder and 5 percent by weight powder particle to 5 percent by weight binder and 95 percent by weight powder particle. Increasing the relative amount of powder particle improves adhesion of the adhered coating layer. The primer may conveniently be comprised of from 10 percent to 90 percent by weight binder and from 90 percent to 10 percent by weight powder particle. Preferably the primer is from 50 percent to 10 percent by weight binder and 50 percent to 90 percent by weight powder particle. Most preferred are the primers with from 30 percent to 40 percent binder and from 70 percent to 60 percent powder particle.

The primer may be coated onto the polymeric film with any conventional process. if the binder is suited for solvent based coatings, a slurry containing binder dissolved in solvent and slurried powder particles may be prepared. The resulting slurry may be coated by conventional knife coating, printing (gravure, screen, and the like), squeeze rolling, spraying, or wire wound rod coating. The solvent is then evaporated and the film is ready for application of the adhered layer. Alternatively, when the binder system suited for hot melt extrusion is selected, the powder particles may be added to resin pellets before melting or to the extrusion liquid after melting and prior to extrusion. Finally, if a thermal or irradiation cure resin is selected for the binder system a slurry containing the liquid resin and powder particles may be coated or printed onto the film and the resin cured. The preferred method of application is gravure printing of a solvent, dissolved binder resin, and slurried powder particles followed by evaporation of the solvent.

The thickness of the dry primer coating on the film may vary from 1 micron to 100 microns. The thickness of the primer coat may conveniently vary from about 1 microns to 50 microns. Preferably the thickness of the primer coating is between 1 microns and 5 microns. Most preferred is a primer thickness of 5 microns.

Particularly preferred films, binders, and powders are commercially available lapping films (e.g., Imperial Lapping film, 3M, St. Paul, MN). These films are polymeric films such as polyester coated with binder and powder particles. The binder is typically a polymeric resin such as a polyester. The powder particles are typically silicon carbide or aluminum oxide. Film coated to a dry thickness from about 10 microns to 50 microns with 15 micron particles (median effective spherical diameter of about 12 microns) silicon carbide in 25 to 50% (weight) polyester resin are preferred.

The adhered layer may be any metal, metal salt, metal oxide, or semiconductor material. The selection depends on the intended use. For electrical conductors, conductive metals, their conductive oxides, and salts and semiconductors are used. The preferred conductive metal, metal salt, system is silver/silver chloride. The preferred semiconductor is graphite. Other conductive metals, salts, oxides and semiconductors are well known to those skilled in the art. Similarly suitable materials for magnetic recording tapes, imaging films, and decorative films are well known to those skilled in the art.

The adhered layer may be applied with any conventional process to any desired thickness. Vapor deposition, sputtering, electroplating, plasma coating, precipitation from solution and mechanical calendering or pressing are all suitable. Application of the coating layer as a slurry or ink is also suitable. For silver and silver chloride the preferred method is vapor deposition of silver to a thickness from about 1,000 Å to 4,000 Å (1.9 gm/m$^2$ to 5.4 gm/m$^2$), preferably about 3,000 Å (4.5 gm/m$^2$ silver and silver ion content) followed by immersion of the silver coated film in a solution containing 0.3% by weight NaClO$_2$, 0.3% by weight HCl, and 99.4% by weight water for 15 seconds. Films prepared in this manner have from about 1.5 g/m$^2$ to about 6 g/m$^2$ total silver content and about 0.3 g/m$^2$ silver chloride. Preferably the film has about 5.4 g/m$^2$ total silver content and about 0.3 g/m$^2$ silver chloride. These composites have appropriate conductivity and electrical coupling between an electrolyte and metal for use as electrical connectors in biomedical electrodes.

For graphite adhered layers, callendaring powdered graphite into the primer layer is preferred. The graphite is coated to a total of 3.0 gm/m$^2$ to 11 gm/m$^2$, preferably 9 gm/m$^2$.

Additional features and advantages of the present invention will be appreciated from the following non-limiting examples.

EXAMPLE 1

Polyester film (polyethylene terephthalate 2 mil. 51 microns thick was coated with primer by the gravure process using a conventional apparatus. The primer was prepared from a mixture of polyester resin 9% weight, 2 micron median equivalent spherical diameter silver flake (49% weight) (the resin and silver being commercially available as silver ink No. 5005, DuPont, Wilmington, Del. 119 grams) and cellosolve acetate (42% weight) (Union Carbide Co., Danbury, Conn. 30 grams) to give a dry coating approximately 90 microinches (2.25 microns) in thickness. The gravure coater had 100 lines per inch (39 lines per centimeter) of an average depth of 0.0034 inches (85 microns). The coated film was weighed to assure uniform wetting and the coating was dried at 107° C. for 5 minutes, passing through a adhered oven at 25 ft/minute (7.6 meters/minute).

The polyester film coated with primer was then coated with a layer of 99.9% silver using a conventional vapor coater, passing the film at 50 ft/minute (15 meters/minute), at a pressure of $1 \times 10^{-5}$ torr. The silver layer was approximately 5000 Å thick with about 4.5 g/m$^2$. The metal coated film was tested directly after coating ($T_o$), after twenty-four hours at ambient conditions ($T_{24}$), and after ten days at ambient conditions ($T_{10}$) by the peel adhesion test (Test Method II below). Four samples were taken. The average peel adhesion values are reported in Table I.

These adhesion values can be compared to those obtained with a composite comprised of the identical polyester film and 5000 Å, 4.5 g/m$^2$ silver vapor deposited without a primer layer. The adhesion results are reported in the "Untreated Film" column of Table I.

Similarly the composition of the present invention shows better adhesion than obtains with a plasma treated film. In this experiment, the gravure coating step was omitted and the surface of the polyester film was plasma treated. The plasma treatment was done in a conventional vapor coater at 4 KV, 250 ma, running the film at 25 ft/minute (7.6 meters/minute), in the presence of oxygen at a pressure of $60 \times 10^{-3}$ torr. The adhesion results are reported in the "Plasma Treated" column of Table I.

TABLE I

| | Peel Force In Grams | | |
|---|---|---|---|
| Time | Primer Coated Film | Untreated Film | Plasma Treated Film |
| $T_0$ | 274 | 38.5 | 30.5 |
| $T_{24}$ | 227 | 26.6 | 32.7 |
| $T_{10}$ | 233 | 0* | 63.2* |

*Patches of delamination were observed

EXAMPLE 2

As in Example 1, polyester film was gravure coated with silver ink in cellosolve acetate, dried, and vapor coated with silver. Samples of the silver-coated film were subjected to peel tests by Test Method II after three ($T_3$) and ten ($T_{10}$) days at ambient conditions. The results, are shown in the "Primer Coated" column of Table II.

Using conditions identical to those reported in Example 1, a polyester film was plasma treated in oxygen before being vapor-coated with silver. The peel test results are reported in the "Plasma Treated" column of Table II.

A polyester film was gravure coated with silver ink in cellosolve acetate and dried in a procedure identical to that of Example 1, but the vapor coat of silver was omitted. The peel test results are reported in the "Primer without Silver" column of Table II.

TABLE II

| | Peel Force in Grams | | |
|---|---|---|---|
| Time | Primer Coated | Plasma Treated | Primer without Silver |
| $T_3$ | 750 | 105 | 650 |
| $T_{10}$ | 488 | 0 | 325 |

EXAMPLE 3

As in Example 1 a polyester film was gravure coated with silver ink comprised of VITEL ® 200 resin mixture with DuPont ® 5005 Silver ink in cellulose acetate, only the amount of silver in the coating solution was varied from zero to 48.8 weight percent. The films were vapor coated with 99.9% silver. The film were tested for peel after two days ($T_2$), using the procedure of Test Method I. The relative proportion of the coating ink, the relative amoutns of any binder and silver the amount of vapor deposit silver and the test results are shown in Table III.

TABLE III

| Sample | Solvent Weight % | Binder Weight % | Silver Weight % | Dry Binder Weight % | Dry Silver Weight % | Vapor Coating Silver in g/m$^2$ | Peel $T_2$ |
|---|---|---|---|---|---|---|---|
| A | 42.9 | 8.3 | 48.8 | 17 | 83 | 1.5 | excellent |
| B | 75 | 25 | 0 | 100 | 0 | 1.0 | peeled |
| C | 68.2 | 22.9 | 8.8 | 83 | 17 | 1.9 | corroded |
| D | 51.2 | 17.8 | 31 | 37 | 63 | 1.2 | excellent |

EXAMPLE 4

In this experiment, polyester film (polyethylene terephthalate) was coated by the gravure process with a coating having a similar composition to the silver ink of Example 1, except that the silver was replaced by small particles of aluminum oxide or silicon carbide. The constituents, relative proportions, and solvents of the primer coats are set out in Table III. In all cases the films were vapor coated with adhered layers of silver in a manner of identical to that of Example 1. All the films were tested for detelamination using the procedure of Test Method I with failures being observed only with the 0.3 micron aluminum oxide.

TABLE IV

| Binder Resin | Powder Particle | Powder to Binder Ratio | Average Particle Diameter Microns | Dry Coating Thickness Microns |
|---|---|---|---|---|
| Polyester | Silicon Carbide | 2:1 | 3 | 12-75 |
| Polyester | Aluminum Oxide | 2:1 | 3 | 12-15 |
| Polyester | Aluminum Oxide | 2:1 | 1 | 8-12 |
| Phenolic | Aluminum Oxide | 2:1 | 0.3 | 8-10 |

EXAMPLE 5

Polyester (polyethylene terephthalate films, 2 mil., 51 microns thick, were sputter etched by the conventional radio frequency bombardment in argon. In this operation, the surface is bombarded with inert gas, i.e., noble gas ions, to remove approximately 200 to 300 nanometers of the surface, and to increase the amplitude of the peaks such that a predominant number of the peaks range in amplitude between 20 and 160 nanometers, the separation of adjacent peaks being not greater than 3 times the maximum amplitude of the peak. The surface is bombarded with argon ions at a pressure of approximately 5 millitorr for a period of 6 minutes. The surface of each film was examined by scanning electron microscope and found to be microscopically rough with hills and valleys spaced about 2000 Å 3000 Å between peaks. These films and control film (untreated) were vapor coated with silver using 99.9% silver in a conventional vapor coater passing the film at 50 ft/min (15 m/min) at a pressure of $1 \times 10^{-5}$ torr. The silver was coated to a thickness of 10,000 Å.

Polyester films identical to those above were sputtered with a nucleating coating of copper using the conventional vapor coating process with a film speed of 10 ft/min (3 m/min) and a pressure of $1 \times 10^{-6}$ torr. The reulting films each had a 60 Å coating of copper and appeared smooth under scanning electron microscope. Samples of the copper nucleated film and control films (untreated) were vapor coated with silver under conditions identical to those above to a thickness of 1000 Å and 5,000 Å.

Each of the silver coated films of this example was tested for delamination in conditions simulating biomedical electrodes (Test Method I). The results are shown in Table V.

TABLE V

| Treatment | Silver Thickness in Å | Day Failure Observed |
|---|---|---|
| Radio Frequency Sputter | 10,000 | $T_1$ |
| Copper nucleated | 5,000 | $T_1$ |
| Control (none) | 10,000 | $T_7$ |
| Copper nucleated | 1,000 | $T_1$ |
| Control | 5,000 | $T_1$ |

EXAMPLE 6

Several films were used to prepare composites of the present invention. In each case the film was coated with primer by using Gravure printing as described in Example 1. The binder and powder particles were polyester and silver flakes with average particle diameter of 2 microns obtained as silver ink from DuPont, Wilmington, Del. (Silver Ink No. 5005). The silver ink was mixed with an equal weight of cellosolve acetate and coated. The cellosolve acetate was evaporated by drying at 107° C. for 5 minutes. The resulting primer coat on the film was 14.5% weight binder, 85.5% weight silver flakes, and about 10 microns thick. Each film, and a control untreated film for each, was vapor coated with silver under conditions identical to those of Example 4 to a thickness of 5000 Å. The films were ethyl vinyl acetate (10 mil, 260 microns) polyester (2 mil, 51 microns), polyethylene (10 mil, 260 microns), polypropylene (4 mil, 104 microns), polycarbonate (4 mil, 104 microns), and polystryene (6 mil, 156 microns).

Each of these composites and the composites of untreated film and silver, was subjected to a peel test. In each peel test a pressure sensitive tape (3M Brand, #600, 3M, St. Paul, MN) was adhered to the silver surface. After twenty-four hours the pressure sensitive adhesive tape was removed by hand. In each instance, the silver delaminated from the untreated film while no adhesion failure was observed with composites of film, primer, and silver.

Each of the silver coated films of this example was tested after twenty four hours for delamination of silver in conditions simulating those found with biomedical electrodes (Test Method I). In each case the primer coated film showed good silver adhesion which the untreated films showed delamination.

Test Method I

A sheet of approximately $3 \times 10$ inches ($7.6 \times 25.4$ cm) of the silver-coated film was used as a test sample. Upon this, a 0.5 inch (1.27 cm) wide strip of conductive adhesive of U.S. Pat. No. 4,524,087 was coated. That adhesive is a swellable, dermally non-irritating conformable cohesive, of an ionic and hydrophilic polymer. The adhesive is derived from an essentially solventless polymerization of a precursor comprised of a water soluble polyhydric alcohol which is liquid at about 20° C., and an ionic unsaturated free radically polymerizable material which is soluble in a polyhydric alcohol. The crosslinking agent is a multifunctional unsaturated free radically polymerizable material. Polymerization is begun with a free radical initiator of either the thermo or photo class. In the electrically conductive adhesive used, the precursors are acrylic acid (15% by weight) and polyacrylic acid (2-5% by weight). The photoinitiator is benzyl dimethyketal 0.07% by weight (available under the trade name Irgacure 651 from Ciba Geigy). The electrolyte and plasticizer system is water (13% by weight) glycerin (68% by weight) and potassium chloride (2% by weight).

The adhesive was laid down as a transfer strip on 57 pound silicon release paper (H. B. Smith), and was rolled into firm contact with a 4.5 lb. (2.0 kg) roller rolled back and forth once at a speed of about 90 inches (220 cm) per minute. To test delamination the adhesive strip was removed by hand at a 180° peel angle. The silver coating was examined to see whether it was intact, or had been pulled off its substrate by the adhesive strip.

Test Method II

A 10 inch $\times$ 1 inch (25.4 cm $\times$ 2.54 cm) test piece of the construction is used. To the metal face of this is attached a strip of ½ inch (1.27 cm) wide adhesive, rolled down, etc., as in Test Method I, with about 5" (13 cm) overlap extending beyond the end of the test specimen.

The specimen itself is attached on its back surface to a metal plate, e.g. by means of double-coated adhesive tape. The assembly is mounted between the jaws of an Instron machine (model #1122), one jaw holding the metal place, one jaw holding the loose end of the adhesive strip, which is doubled back on itself so as to give an 180° peel when the jaws are moved apart.

The jaws of the machine are operated at a speed of 5 inches/minute (12.7 cm/minute). The peel force is measured and the physical integrity of the silver coating is observed.

What is claimed is:

1. A biomedical electrode conductor, said conductor comprising:
   a conformable polymeric film;
   a primer coated on a surface of the film, the primer comprising from about 1 to 40 weight percent (dry) binder and from about 60 to 99 weight percent (dry) powder particles, the powder particles having a median effective spherical diameter of from about 2 microns to about 100 microns, the dry thickness of the primer being between about 1 micron and about 100 microns; and
   a layer of metal, metal oxide, metal salt, semiconductor material, or mixture thereof adhered to the surface of the primer opposed to the film;
   wherein said biomedical electrode conductor renders a biomedical electrode capable of recovering from polarization potentials imposed during defibrillation procedures.

2. The biomedical electrode conductor of claim 1 wherein the powder particles are selected from the group consisting of conductive metals, their oxides and salts; metal coated microspheres; carbon coated microspheres; magnetic metals, their oxides and salts; clays; silicates; and mixtures thereof.

3. The biomedical electrode conductor of claim 2 wherein the binder is a polyester or polyurethane resin.

4. The biomedical electrode conductor of claim 1 wherein the powder particles are selected from the group consisting of silver, silver salts, zinc, zinc oxide, zinc salts, tin, tin oxide, tin salts, aluminum, aluminum oxide, aluminum salts, silicon, silicon carbide, silicon oxides, silicon salts, graphite, and combinations thereof.

5. The biomedical electrode conductor of claim 4 wherein the binder is a polyester or polyurethane resin.

6. The biomedical electrode conductor of claim 1 wherein the binder is a polyester or polyurethane resin.

7. The biomedical electrode conductor of claim 1 wherein the film is a polyester film, the powder particles are silicon carbide with a median effective spherical diameter between about 10 microns and about 20 microns, and the binder is a polyester resin.

8. The biomedical electrode conductor of claim 7 wherein the adhered layer comprises a mixture of silver and silver chloride and has at least about 1.5 grams per square meter of silver and at least about 0.3 grams per square meter of silver chloride.

9. The biomedical electrode conductor of claim 7 wherein the adhered layer comprises a mixture of silver and silver chloride and has at least about 5.4 grams per square meter of silver and at least about 0.3 grams per square meter of silver chloride.

10. The biomedical electrode conductor of claim 7 wherein the adhered layer comprises graphite and has at least about 3 grams per square meter of graphite.

11. The biomedical electrode conductor of claim 1 wherein the film is a polyester film, the powder particles are silver with a median effective spherical diameter between about 10 microns and about 15 microns, and the binder is a polyester resin.

12. The biomedical electrode conductor of claim 10 wherein the adhered layer comprises a mixture of silver and silver chloride and has at least about 1.5 grams per square meter of silver and at least about 0.3 grams per square meter of silver chloride.

13. The biomedical electrode conductor of claim 10 wherein the adhered layer comprises a mixture of silver and silver chloride and has at least about 5.4 grams per square meter of silver and at least about 0.3 grams per square meter of silver chloride.

14. The biomedical electrode conductor of claim 1 wherein the film is a polyester film, the powder particles are graphite with a median effective spherical diameter of about 2 microns, the binder is a polyester resin, and the adhered layer comprises graphite and has at least about 3 grams per square meter of graphite.

15. A biomedical electrode conductor as defined in claim 1 wherein the powder particles have a median effective spherical diameter of from about 2 microns to about 50 microns.

16. A biomedical electrode conductor as defined in claim 1 wherein the powder particles have a median effective spherical diameter of from about 2 microns to about 40 microns.

17. A biomedical electrode conductor as defined in claim 1 wherein the powder particles have a median effective spherical diameter of from about 2 microns to about 20 microns.

18. A biomedical electrode conductor as defined in claim 1 wherein the adhered layer has a thickness of from about 1000 Angstroms to about 4000 Angstroms.

19. A biomedical electrode conductor as defined in claim 1 wherein the powder particles have a median effective spherical diameter of from about 5 microns to about 100 microns.

20. A biomedical electrode conductor as defined in claim 1 wherein the powder particles have a median effective spherical diameter of from about 5 microns to about 20 microns.

21. A biomedical electrode conductor as defined in claim 1 wherein the primer comprises from about 30 to 40 weight percent (dry) binder and from about 60 to 70 weight percent (dry) powder particles.

22. A biomedical electrode conductor as defined in claim 1 wherein the polymeric film comprises polyester.

23. A biomedical electrode conductor as defined in claim 1 wherein the binder comprises a polyester resin.

24. A biomedical electrode conductor as defined in claim 1 wherein the powder particles comprise silicon carbide.

25. A biomedical electrode conductor as defined in claim 1 wherein the adhered layer comprises a mixture of silver and silver chloride.

* * * * *